US009683872B2

(12) United States Patent
Noe

(10) Patent No.: US 9,683,872 B2
(45) Date of Patent: Jun. 20, 2017

(54) WATER-INGRESS LABEL USING A DOUBLE COATING CAPSULE STRUCTURE

(71) Applicant: QL CO., LTD., Gyeonggi-Do (KR)

(72) Inventor: Ye-Sol Noe, Seoul (KR)

(73) Assignee: QL CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/342,663

(22) PCT Filed: Sep. 20, 2012

(86) PCT No.: PCT/KR2012/007517
§ 371 (c)(1),
(2) Date: Mar. 4, 2014

(87) PCT Pub. No.: WO2013/042945
PCT Pub. Date: Mar. 28, 2013

(65) Prior Publication Data
US 2014/0224170 A1   Aug. 14, 2014

(30) Foreign Application Priority Data

Sep. 20, 2011 (KR) .................. 10-2011-0094448
Jan. 25, 2012 (KR) .................. 10-2012-0007467
Sep. 17, 2012 (KR) .................. 10-2012-0102611

(51) Int. Cl.
*G01D 7/00*     (2006.01)
*G01M 3/00*     (2006.01)
(Continued)

(52) U.S. Cl.
CPC ............. *G01D 7/005* (2013.01); *B32B 5/022* (2013.01); *B32B 29/002* (2013.01); *C09D 5/00* (2013.01);
(Continued)

(58) Field of Classification Search
CPC .......... G01D 7/00; G01D 7/005; G01M 3/00; G01N 21/81; G01N 31/22; G01N 31/222; G09F 3/00; G09F 3/02; G09F 3/0291
(Continued)

(56) References Cited

U.S. PATENT DOCUMENTS 7,105,225 B2 *   9/2006   Birkholz .................. B32B 7/12
                                                    428/343
7,732,046 B2 *   6/2010   LaBrosse ................. B32B 7/12
                                                    428/343

FOREIGN PATENT DOCUMENTS

JP     7-140078 A       6/1995
JP     7-334082 A      12/1995
(Continued)

OTHER PUBLICATIONS

International Searching Authority, International Search Report in PCT/KR2012/007517 dated Mar. 18, 2013.

*Primary Examiner* — R. A. Smith
(74) *Attorney, Agent, or Firm* — IPLA P.A.; James E. Bame

(57) ABSTRACT

A water-ingress label using a double coating capsule structure includes a water absorbent layer which is formed from any one of paper, synthetic paper, non-woven fabric, synthetic non-woven fabric, Korean paper or an absorbent coating for absorbing water; an ink layer which is formed on the back surface of the water absorbent layer as an ink having a double coating capsule structure including a colorant selected from any one or a plurality of water-soluble dyes, pigments, metallic silica, metallic oxides and mica together with a hydrophilic/water-absorbing halogen-free resin; and an ink barrier layer having a damp-proofing and water-proofing function, which is formed on the back surface of the ink layer and prevents leaking, into the back
(Continued)

surface of the ink layer, of the colorant selected from any one or more of water-soluble dyes, pigments, metallic silica, metallic oxides and mica.

14 Claims, 2 Drawing Sheets

(51) Int. Cl.
    *G01N 21/81*     (2006.01)
    *G09F 3/02*     (2006.01)
    *B32B 5/02*     (2006.01)
    *B32B 29/00*     (2006.01)
    *C09D 7/12*     (2006.01)
    *C09D 11/037*     (2014.01)
    *C09D 11/10*     (2014.01)
    *C09D 11/50*     (2014.01)
    *C09D 5/00*     (2006.01)

(52) U.S. Cl.
    CPC .......... *C09D 7/1291* (2013.01); *C09D 11/037* (2013.01); *C09D 11/10* (2013.01); *C09D 11/50* (2013.01); *G01M 3/00* (2013.01); *G01N 21/81* (2013.01); *G09F 3/02* (2013.01); *B32B 2255/02* (2013.01); *B32B 2255/12* (2013.01); *B32B 2255/28* (2013.01); *B32B 2307/4023* (2013.01); *B32B 2307/706* (2013.01); *B32B 2307/728* (2013.01); *B32B 2307/7265* (2013.01); *B32B 2519/00* (2013.01); *Y02P 20/149* (2015.11)

(58) Field of Classification Search
    USPC .................................................. 116/200, 216
    See application file for complete search history.

(56) References Cited

FOREIGN PATENT DOCUMENTS

| | | |
|---|---|---|
| JP | 2001-312207 A | 11/2001 |
| WO | 2005/049753 A1 | 6/2005 |

* cited by examiner

Fig. 1 — Prior Art —
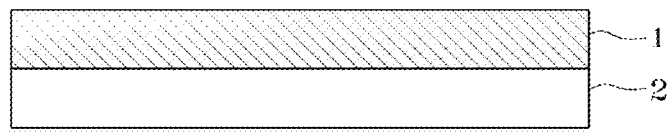
Fig. 2 — Prior Art —
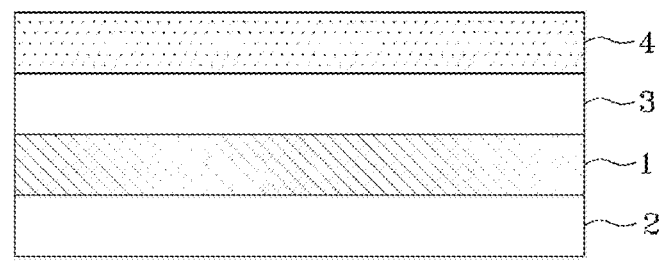
Fig. 3
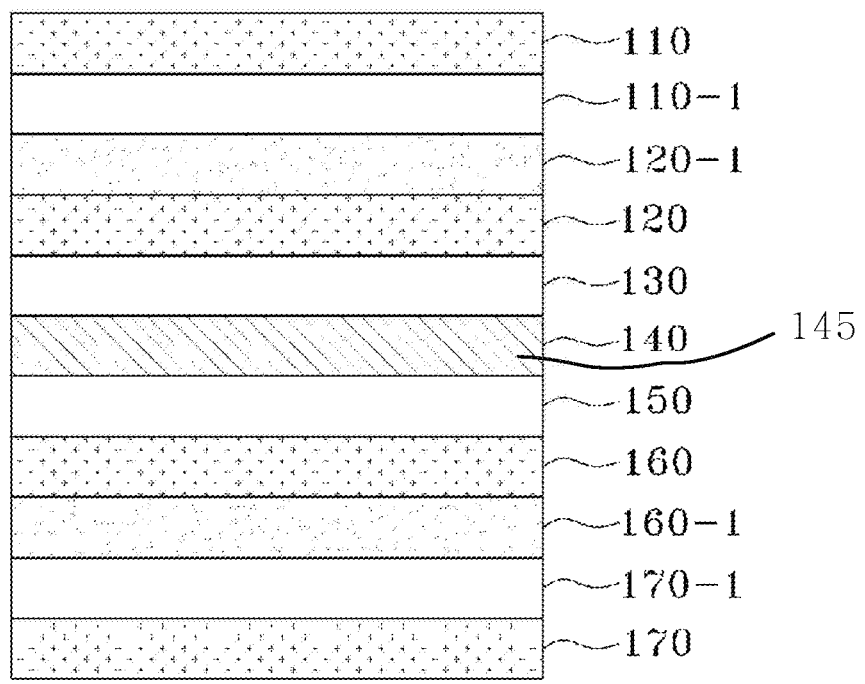

WATER-INGRESS LABEL USING A DOUBLE COATING CAPSULE STRUCTURE

CROSS REFERENCE TO RELATED APPLICATIONS

This application is a National Stage of International Application No. PCT/KR2012/007517 filed Sep. 20, 2012, claiming priority based on Korean Patent Application Nos. 10-2011-0094448 filed Sep. 20, 2011, 10-2012-0007467 filed Jan. 25, 2012 and 10-2012-0102611 filed Sep. 17, 2012, the contents of all of which are incorporated herein by reference in their entirety.

FIELD OF THE INVENTION

The present invention relates to a water-ingress label using a double coating capsule structure, more particularly, a water-ingress label using a double coating capsule structure which can accurately check whether or not the ingress of water ingress has occurred even over a narrow area by allowing two color changes in contrast to existing color change by means of ink having a double coating capsule structure.

DESCRIPTION OF THE RELATED ART

As a conventional water-ingress label for indicating the ingress of water to a product, a spreading-type label has been produced by mixing coloring colorant as ink able to indicating the ingress of water and water-soluble resin.

More specifically, referring to FIG. 1, on a water-soluble resin (1) such as water-absorbent paper etc., an ink layer (2) is formed which is formed of water-soluble ink formed of water-soluble red dyes or pigments etc, with a pattern such as checks, dots etc. printed on the ink layer. Therefore, if the label contacts with the water, the resin is solved together with the red ink to spread in the paper, whereby the ingress of water can be checked by the spread state.

It is inconsistent in that there is almost no spread when the amount of the absorbed water is small and the ink is completely absorbed and thus its color disappear when the amount is large. In addition, since printed red ink also spreads also in a condition of high temperature and humidity, there are many problems in checking whether the ingress of water has occurred, only based on the degree of spread, and thus disputes continually arise.

Furthermore, as various electronic products get compact, a checking area of the water-ingress label also becomes very small (for example, a circle of 2 mm). Therefore, there is a problem that it is difficult to check the spread by the pattern such as checks, dots etc.

In addition, there is a problem that the water-ingress label is sensitive to humidity, therefore, a coating layer is peeled off in case of high temperature and humidity, whereby reliability decrease and dyes escape toward an upper side of the label paper of the water-ingress label, therefore, the dyes must be protected by forming a dye-protecting layer, so that production processes increase and thus additional production time and production cost are required.

Meanwhile, for overcoming these drawbacks, a conventional water-ingress label in FIG. 2 adopts a way wherein white water-soluble ink (3) is applied to a white water-absorbent paper and ink of red water-soluble dye is applied to upper surface with the ink applied thereon and then lamination is performed to form a coating layer (4). Namely, it is a way wherein after the water is absorbed by a water-absorbent and water-soluble resin (1), ink layer (2) of water-soluble red dye is solved and the ink passes again through white color of the water-absorbent and water-soluble resin (1) for concealment to spread out up to paper.

However, also in case of such a way, there is a problem that, if a lot of moistures penetrate and in bad condition of high temperature and humidity etc., the red color penetrates into the white color by itself, whereby the color is changed.

Meanwhile, there is a need for development of a product which solves the problems of prior art and can replace a product produced from vinyl chloride that is mainly used for conventional water-ingress label products, as the product produced from vinyl chloride can no longer be used due to environmental regulations.

DOCUMENTS OF RELATED ART

1. Water-ingress label (Korean Patent Application No. 10-2004-0111204)
2. Screw sealing device with water-ingress indication label of electronic products (Korean Utility Model Application No. 20-2003-0033671)

SUMMARY OF THE INVENTION

The present invention is intended to solve the above-mentioned problems, and its object is to provide a water-ingress label using a double coating capsule structure which allows one to accurately know whether or not the ingress of water into a water-ingress label attached to a product has occurred, while preventing the change of color by means of crosslinking of the double coating capsule even in case of the permeation of a lot of moistures and in a bad condition of high temperature and humidity.

Furthermore, another object of the present invention is to provide a water-ingress label using a double coating capsule structure which can accurately check whether or not the ingress of water ingress has occurred even over a narrow area, by adopting the double coating capsule structure, exhibiting a strong damp-proofing property owing to ink barrier layer and double-sided water-proof layer and allowing two color changes in contrast to existing spread of color.

In addition, yet another object of the present invention is provide a halogen-free water-ingress label using a double coating capsule structure for providing a product made halogen-free in order to solve a problem that products produced from vinyl chloride can no longer be used due to environmental regulations, although vinyl chloride is conventionally used for the water-ingress label products.

However, objects of the present invention are not restricted to the above-mentioned objects, and another objects not mentioned may be understood from the following description by a person skilled in the art.

In order to achieve the above-mentioned objects, a water-ingress label using a double coating capsule structure according to an exemplary embodiment of the present invention comprises a water-absorbent layer formed on a back surface of the first water-proof layer from any one of paper, synthetic paper, nonwoven fabric, synthetic nonwoven fabric, Korean paper and an absorbent coating in order to absorb the water from the outside; an ink layer formed by printing, on a back surface of the water-absorbent layer, an ink with a double coating capsule structure comprising a colorant consisting of any one or plural ones of water-soluble dyes, pigments, metal, silica, metallic oxides and mica, and a hydrophilic water-absorbent halogen-free resin; and an ink barrier layer having a damp-proofing and water-proofing function, which is formed on a back surface of the ink layer and prevents leaking, through the back surface of the ink layer, of the colorant of any one or plural ones of the water-soluble dyes, pigments, metal, silica, metallic oxides and mica.

In a water-ingress label using a double coating capsule structure according to another exemplary embodiment of the present invention, the double coating capsule is comprised of 15~35 wt. % of the colorant consisting of any one or plural ones of the water-soluble dyes, pigments, metal, silica, metallic oxides and mica; 15~25 wt. % of the hydrophilic water-absorbent halogen-free resin; and 35~69 wt. % of solvent, and formed by crosslinking by means of 1~5 wt. % of crosslinking agent consisting of any one or plural ones of polyisocyanate-based resin, amino-based resin, aziridine-based resin, amide-based resin and epoxy-based resin.

In a water-ingress label using a double coating capsule structure according to another exemplary embodiment of the present invention, the ink of the ink layer is formed of 15~35 wt. % of the double coating capsule; 15~25 wt. % of the halogen-free resin comprising resin consisting of any one or plural ones of polyamide-based resin, polyacryl-based resin, cellulose-based resin, polyester urethane-based resin, acryl-styrene copolymer resin and epoxy-based resin mixed with the colorant consisting of any one or plural ones of the dyes, pigments, metal, silica, metallic oxides and mica; and 40~70 wt. % of the solvent.

In a water-ingress label using a double coating capsule structure according to another exemplary embodiment of the present invention, the double coating capsule is formed in such a way that the colors of its inner part and outer part are different form each other by mixing the halogen-free resin and outer colorant (for example, white) having a different color from the color (for example, red) of an inner colorant, which is formed of water-soluble dye, and consisting of any one or plural ones of the dyes, pigments, metal, silica, metallic oxides and mica and crosslinking the resulting mixture with the upper surface of the inner colorant (for example, red), thereby obtaining physical properties of solvent-resistant, damp-proofing and water-soluble properties and forming an outer color layer (for example, white), namely, the inner part of the double coating capsule has the color (for example, red) of the inner colorant and the outer part of the double coating capsule has the color (for example, white) of the outer colorant.

In a water-ingress label using a double coating capsule structure according to another exemplary embodiment of the present invention, the double coating capsule is resistant to humidity, however, if absorbing the water, is expanded and thus broken, and then the colorant contained within the double coating capsule colors the layers, and thus indication of the ingress of water is realized.

In a water-ingress label using a double coating capsule structure according to another exemplary embodiment of the present invention, the halogen-free resin of the double coating capsule is formed of any one or plural ones of polyacrylamide, polycarboxylic acid, EPOCROS, polyvinyl alcohol, methyl cellulose, carboxymethyl cellulose, and poly vinyl pirrolidone.

The water-ingress label using a double coating capsule structure according to another exemplary embodiments of the present invention further comprises a first water-proof layer formed on a front surface of a water-absorbent layer and second water-proof layer formed on a back surface of the ink barrier layer so that the water is absorbed from the outside via lateral sides of the water-absorbent layer.

The water-ingress label using a double coating capsule structure according to yet another exemplary embodiments of the present invention further comprises a first durable coating layer formed on a front surface of a first water-proof layer and a second durable coating layer formed on a back surface of a second water-proof layer so that the first water-proof layer and the second water-proof layer could withstand an environment such as friction, scratching etc. and also external shock.

The water-ingress label using a double coating capsule structure according to an exemplary embodiments of the present invention provides an effect that it makes possible to accurately know whether or not the ingress of water into a water-ingress label attached to a product has occurred, while preventing the change of color even in case of the permeation of a lot of moistures and in a bad condition of high temperature and humidity.

Furthermore, the water-ingress label using a double coating capsule structure according to another exemplary embodiments of the present invention provides a halogen-free product that solves a problem that products produced from vinyl chloride can no longer be used due to environmental regulations, although the vinyl chloride is used for conventional water-ingress label products.

In addition, the water-ingress label using a double coating capsule structure according to yet another exemplary embodiments of the present invention provides an effect that it makes possible to accurately check whether or not the ingress of water ingress has occurred even over a narrow area by exhibiting a strong damp-proofing property owing to the ink barrier layer and double-sided water-proof layer and allowing two color changes in contrast to existing color change.

BRIEF DESCRIPTION OF THE DRAWINGS

FIGS. 1 and 2 are view illustrating structures of conventional water-ingress labels.

FIG. 3 is a view illustrating a water-ingress label using a double coating capsule structure according to an exemplary embodiment of the present invention.

DETAILED DESCRIPTION OF THE EMBODIMENTS

Figure 4:
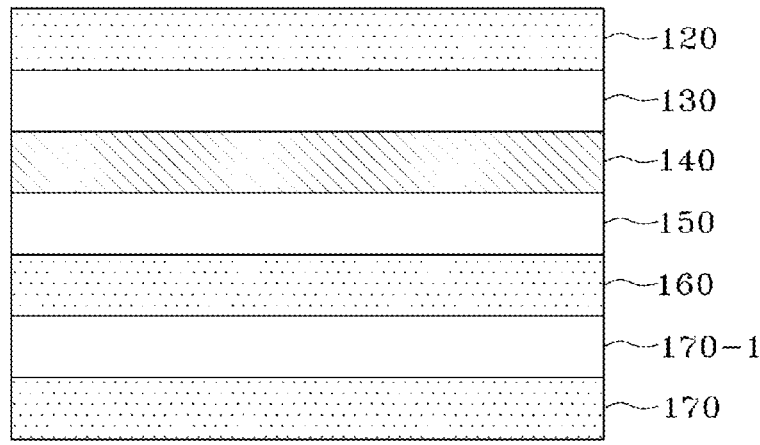
FIGS. 4 to 6 are view illustrating constructions of water-ingress labels according to another exemplary embodiments of the present invention.

In the following, preferred exemplary embodiments of the present invention will be described in detail with reference to the attached drawings. In the following description of the present invention, if it is determined that detailed description of related known functions or construction unnecessarily obscures the gist of the present invention, the detailed description thereof will be omitted.

For the color used for a double coating capsule of the water-ingress label according to the present invention, various colors may be selectively applied depending on a person skilled in the art. In the following, the double coating capsule of the present invention will be described with highly-visible red color as color used for the double coating capsule.

FIG. 3 is a view showing a water-ingress label using a double coating capsule structure according to an exemplary embodiment of the present invention. Referring to FIG. 3, the water-ingress label comprises a first release layer (110), a first adhesive layer (110-1), a first durable coating layer (120-1), a first water-proof layer (120), a water-absorbent layer (130), an ink layer (140), an ink barrier layer (150), a second water-proof layer (160), a second durable coating layer (160-1), a second adhesive layer (170-1) and a second release layer (170).

The first release layer (110) is separated before the water-ingress label is attached to various products by means of the first adhesive layer (110-1).

The first adhesive layer (110-1) is formed on a back surface of the first release layer (110), and provides adhesive force for attachment to various products after the first release layer (110) is separated.

The first durable coating layer (120-1) is formed on a back surface of the first adhesive layer for protection from the outside environment.

The first water-proof layer (120) allows the water to be absorbed from the outside only via lateral sides of the water-absorbent layer (130), the ink layer (140), and the ink barrier layer (150) of the water-ingress label, not via plane surface (front surface, back surface) thereof, and thus serves to prevent the change of color even in a bad condition of high temperature and humidity in case of penetration of a lot of moistures.

The first water-proof layer (120) is formed between the first durable coating layer (120-1) and the water-absorbent layer (130).

For the water-absorbent layer (130), paper, synthetic paper, nonwoven fabric, synthetic nonwoven fabric, or Korean paper having a good absorbability for water is used for absorbing external water. Alternatively, the water-absorbent layer with absorptive coating applied thereon is formed between the first water-proof layer (120) and the ink layer (140).

The water-absorbent paper is a cellulose-based paper, and its weight is preferably 65 g/m$^2$.

The ink layer (140) is formed by printing, on the back surface of the water-absorbent layer (130), an ink with a double coating capsule structure (145) comprising a colorant consisting of any one or plural ones of dyes, pigments, metal, silica, metallic oxides and mica, and a hydrophilic water-absorbent halogen-free resin.

The ink barrier layer (150) is formed on the back surface of the ink layer (140) to prevent leaking, through the back surface of the ink layer (140), of the colorant consisting of any one or plural ones of the water-soluble dyes, pigments, metal, silica, metallic oxides and mica, and has a damp-proofing and water-proofing function.

Furthermore, the second water-proof layer (160) is formed on a back surface of the ink barrier layer (150) in order to reinforce the ink barrier layer (150), and the second durable coating layer (160-1) is formed on a back surface of the second water-proof layer (160) to protect the second water-proof layer from the outside environment, and the second adhesive layer (170-1) is formed on a back surface of the second durable coating layer (160-1) for attachment to various products, and the second release layer (170) is formed on a back surface of the second adhesive layer (170-1).

In case that the water-absorbent layer (130) consists of a hydrophilic absorptive coating able to well absorb the water, resin of the ink is halogen-free urethane resin combined with acryl-based resin and polyester-ether copolymer resin, and is formed of any one or plural ones of the acryl-based resin, polyester-ether copolymer resin and urethane resin, each of which is comprised of hydrophilic monomer, water-absorbent monomer and hydrophobic monomer for increasing the strength of coating film and preventing water solubility thereof.

The absorptive coating ink for forming the water-absorbent layer (130) is formed by mixing 15~35 wt. % of the hydrophilic water-absorbent halogen-free resin with 0~15 wt. % of the colorant consisting of any one or plural ones of the dyes, pigments, metal, silica, metallic oxides and mica, 0.1~5 wt. % of hardening agent, and 45~84.9 wt. % of solvent.

For the solvent, aromatic solvent, i.e., toluene, xylene, cresol etc., alcoholic solvent, i.e., methanol, ethanol, propanol, butanol etc., ketonic solvent, i.e., metyletylketon, metylisobutylketon, cyclohexanon etc., or esteric solvent, i.e., ethyl acetate, butyl acetate, isobutyl acetate, isophorone etc., or mixed solution thereof is used.

Furthermore, the water-absorbent layer (130) may have a hydrophilic water-soluble coating according to circumstances, and the halogen-free resin is formed of any one of polyvinyl alcohol, polyvinyl pyrolidone, polyethylen glycol and celullose-based material, or combination of plural ones thereof.

The hydrophilic water-soluble halogen-free ink of the water sorbent layer (130) is formed by mixing 15~35 wt. % of the selected hydrophilic water-soluble resin with 0~15 wt. % of the colorant consisting of any one or plural ones of the dyes, pigments, metal, silica, metallic oxides and mica, or 0.1~5 wt. % of the hardening agent, or 45~84.9 wt. % of alcohol or deionized water solvent, or mixture thereof.

On the other hand, the resin of the water-absorbent layer (130) is formed by mixing any one or plural ones of the water-absorbent coating resins and any one or plural ones of the water-soluble coating resins.

Also, any one or plural ones of the water-absorbent coating resin and the water-soluble coating resin is(are) selected to be mixed with the resin of the ink layer (140).

Meanwhile, amino resin, urethane hardening agent, aziridine, epoxy resin or amine-based hardening agent etc. is properly used for adjusting the strength and absorbability of the coating film of the water-absorbent layer (130).

The thickness of the absorptive coating of the water-absorbent layer (130) is 10~100 µm, preferably 60~80 µm.

Furthermore, as an another exemplary embodiment of the present invention, in case of applying an absorptive coating for forming the water-absorbent layer (130), since a substrate for the absorptive coating is required if an absorptive paper as the water-absorbent layer (130) is omitted, any one of the front surface of the first durable coating layer (120-1), the first durable coating layer (120-1), the first water-proof layer (120), the ink barrier layer (150), the second water-proof layer (160), the second durable coating layer (160-1) and the back surface of the second durable coating layer (160-1) must be formed by using a film or a release film as substrate for replacing the absorptive paper.

The film is transparent, translucent or opaque, and a selected film is formed with or without a color or with metallic (including metal deposition) color.

Meanwhile, for a strong damp-proofing property of the water-absorbent layer (130), a double water-absorbent layer (130) with strong damp-proofing/water-absorbing properties may be formed by mixing 0.2~1 wt. % of the urethane hardening agent, more preferably, polyisocyanate-based hardening agent with the resin or ink of the water-absorbent layer (130) to change physical properties and coating, with the resulting mixture thus obtained, a front or back surface of paper, synthetic paper, nonwoven fabric, synthetic nonwoven fabric or Korean paper with a coating thickness of 3~5 μm.

The ink layer (140) is formed between the water-absorbent layer (130) and the ink barrier layer (150), wherein the ink layer is formed on an entire surface or by printing patterns.

The ink of the ink layer (140) is of the hydrophilic water-absorbent halogen-free resin; the colorant consisting of any one or plural ones of dyes, pigments, metal, silica, metallic oxides and mica; the double coating capsule; and the solvent.

The ink layer (140) is formed by being printed on the back surface of the water-absorbent layer (130).

Inner colorant of the double coating capsule is formed of any one or plural ones of the water-soluble dyes, pigments, metal, silica, metallic oxides and mica, and outer colorant is formed by mixing and crosslinking the colorant consisting of any one or plural ones of the dyes, pigments, metal, silica, metallic oxides and mica with, as halogen-free resin, resin consisting of any one or plural ones of polyacrylamide, polycarboxylic acid, EPOCROS (a brand name of oxazoline-functional polymer), polyvinyl alcohol, methyl cellulose, carboxymethyl cellulose, and poly vinyl pirrolidone or other synthetic resin to obtain solvent-resistant damp-proofing and water-soluble properties.

For crosslinking agent, any one or plural ones of polyisocyanate-based resin, amino-based resin, aziridine-based resin, amide-based resin and epoxy-based resin is(are) used.

For the water-ingress label using the double coating capsule structure of the present invention, its damp-proofing property and time when it is broken upon contact with the water can be adjusted by means of physical properties and thickness of the resin of the double coating capsule, the crosslinking agent and the degree of crosslink.

If absorbing the water, the completed double coating capsule is expanded, and thus a surface of the capsule is broken and then the colorant contained in the capsule leaks out to be absorbed by the ink layer (140) and the water-absorbent layer (130), thereby coloring these layers, whereby indication of the ingress of water is irreversibly realized.

The double coating capsule is formed by properly crosslinking 15~35 wt. % of the colorant consisting of any one or plural ones of the water-soluble dyes, pigments, metal, silica, metallic oxides and mica; 15~25 wt. % of the hydrophilic water-absorbent halogen-free resin; and 35~69 wt. % of the solvent by means of 1~5 wt. % of the crosslinking agent.

The ink for forming the ink layer (140) used herein comprises and is formed of the colorant protected by 15~35 wt. % of the water-soluble double coating capsule, 15~25 wt. % of the hydrophilic, water-absorbent and halogen-free resin, and 40~70 wt. % of the solvent.

For the solvent, aromatic solvent, i.e., toluene, xylene, cresol etc., alcoholic solvent, i.e., methanol, ethanol, propanol, butanol etc., ketonic solvent, i.e., metyletylketon, metylisobutylketon, cyclohexanon etc., or esteric solvent, i.e., ethyl acetate, butyl acetate, isobutyl acetate, isophorone etc., or mixed solution thereof is used.

More particularly, the ink of the ink layer (140) is formed of 15~35 wt. % of the double coating capsule; 15~25 wt. % of the halogen-free resin comprising resin consisting of any one or plural ones of polyamide-based resin, polyacryl-based resin, cellulose-based resin, polyester urethane-based resin, acryl-styrene copolymer resin and epoxy-based resin mixed with the colorant consisting of any one or plural ones of the dyes, pigments, metal, silica, metallic oxides and mica; and 40~60 wt. % of the solvent.

Meanwhile, the interior and surface of the double coating capsule, the ink layer (140) of the ink comprising the double coating capsule, the water-absorbent layer (130), the ink barrier layer (150), the first water-proof layer (120), the second water-proof layer (160), the first durable coating layer (120-1) and the second durable coating layer (160-1) etc. are each diversely transparent or metallic, or have a color, and various colors may be realized and used.

The color of the inner colorant of the double coating capsule, the color of the outer colorant as a surface of the double coating capsule, and the color of the resin of the ink layer containing the double coating capsule must be different from each other, however, the color of the outer colorant as a surface of the double coating capsule, and the color of the resin of the ink layer containing the double coating capsule may be the same or different from each other, thus various colors may be realized and selectively used.

For a more specific embodiment, the ink of the ink layer (140) is completed by mixing 15~25 wt. % of the hydrophilic water-absorbent halogen-free resin mixed with white pigment and other colorant; 40~70 wt. % of the solvent; and 15~35 wt. % of the double coating capsule which is formed by mixing the halogen-free resin and outer colorant (for example, white) having a different color from the color (for example, red) of an inner colorant, which is formed of the water-soluble dye, and consisting of any one or plural ones of the dyes, pigments, metal, silica, metallic oxides and mica and crosslinking a mixture thus obtained with the upper surface of the inner colorant (for example, red), thereby obtaining physical properties of solvent-resistant, damp-proofing and water-soluble properties and forming an outer color layer (for example, white), namely, the interior of the double coating capsule has the color (for example, red) of the inner colorant and the exterior of the double coating capsule has the color (for example, white) of the outer colorant, whereby the colors of the interior and the exterior are different form each other.

Meanwhile, the red color of the inner colorant and the white color of the outer colorant as exemplarily described above may be variably applied depending on user.

The completed ink layer (140) containing the completed double coating capsule is seen white with the naked eyes and is resistant to humidity, however, if the ink contacts with the water, the water penetrates into the water-absorbent layer (130) to reach the ink layer (140), and the water permeates into the white hydrophilic water-absorbent resin constituting the ink layer (140) and at the same time the water-soluble double coating capsule is broken and thus red color leaks out to be absorbed by the ink layer (140) and the water-absorbent layer (130) and then color the layers, whereby the irreversible water-ingress label is completed wherein a change from white color to red color take places.

Alternatively, the water absorbed by the water-absorbent layer (130) permeates into the hydrophilic water-absorbent ink layer (140), thus the double coating capsule is broken and the ink layer (140) itself is changed to red color, whereby the irreversible water-ingress label is completed wherein a change from white color to red color can be recognized also in the direction of the second water-proof layer (160).

At this time, it is preferred that more vivid color permeating into the color-changed ink layer (140) and the water-absorbent layer (130) can be recognized by printing dots, checks, or various patterns, rather than applying the ink layer (140) on an entire surface, and it is more preferable to increase the content of the double coating capsule.

The thickness of the ink layer (140) is preferably 5~50 μm, more preferably, 10~20 μm. If the thickness is less than 5 μm, the color is not vivid. The size of particles of the double coating capsule mixed is preferably 2~30 μm, more preferably, 5~10 μm.

The ink barrier layer (150) formed on the back surface of the ink layer (140) serves to allow the colorant of the double coating capsule leaking out to be absorbed only by the water-absorbent layer (130) if the color of the colorant absorbed by the water-absorbent layer (130) is not vivid.

The ink layer (140) is not only formed on the back surface of the water-absorbent layer (130), but also on the front surface thereof, if necessary, to be used.

Lamination or coating is performed on opposite sides of the water-absorbent layer (130) and ink barrier layer (150), and thus the first water-proof layer (120) is formed on a upper surface and the second water-proof layer (160) is formed on a lower surface.

The halogen-free ink of the ink barrier layer (150), the first water-proof layer (120) and the second water-proof layer (160) is formed by mixing 15~35 wt. % of resin consisting of any one or plural ones of acryl resin, polyurethane resin, polystyrene resin, polyester resin, epoxy resin, silicone resin, polyethylene terephthalate resin and polypropylene resin; 0~15 wt. % of the colorant consisting of any one or plural ones of the dyes, pigments, metal, silica, metallic oxides and mica; and 50~85 wt. % of the solvent.

It is preferred that the thickness of the ink barrier layer (150) is 5 μm or more and the thickness of the first water-proof layer (120) and the second water-proof layer (160) is 10 μm or more.

Meanwhile, if the first water-proof layer (120) and the second water-proof layer (160) are formed by lamination, a laminating film is transparent, translucent or opaque, and a selected laminating film is formed with or without a color or with metallic (including metal deposition) color.

The thickness of the laminating film is preferably 16~50 μm.

In order for the first water-proof layer (120) and the second water-proof layer (160) to withstand a harsh environment such as friction, scratching etc. and also external shock, the first durable coating layer (120-1) is formed on the front surface of the first water-proof layer (120) and the second durable coating layer (160-1) is formed on the back surface of the second water-proof layer (160).

The durable coating ink for forming the first durable coating layer (120-1) and the second durable coating layer (160-2) is formed by mixing 15~35 wt. % of the halogen-free urethane resin able to easily protect the surface and block the moisture with 0~15 wt. % of the colorant consisting of any one or plural ones of the dyes, pigments, metal, silica, metallic oxides and mica; 1~5 wt. % of the hardening agent; and 45~84 wt. % of the solvent.

Furthermore, the resin of the ink of the first durable coating layer (120-1) and the second durable coating layer (160-2) is the halogen-free urethane resin combined with acryl-polyester resin, and is formed of any one or plural ones of acryl resin, polyester resin, epoxy resin, UV resin, polyether resin, silicone resin and unsaturated polyester resin.

Furthermore, for enhancing the durability, amino resin, urethane hardening agent, aziridine, epoxy resin or amine-based hardening agent etc. is properly used for the resin of the first durable coating layer (120-1) and the second durable coating layer (160-2), and, suitably, 1~5 wt. % of the urethane hardening agent is preferred.

For the solvent, aromatic solvent, i.e., toluene, xylene, cresol etc., alcoholic solvent, i.e., methanol, ethanol, propanol, butanol etc., ketonic solvent, i.e., metyletylketon, metylisobutylketon, cyclohexanon etc., or esteric solvent, i.e., ethyl acetate, butyl acetate, isobutyl acetate, isophorone etc., or mixed solution thereof is used.

The thickness of the first durable coating layer (120-1) and the second durable coating layer (160-2) is preferably 5~10 μm.

Meanwhile, depending on the required degree of environment, any one or plural ones of the first durable coating layer (120-1), the first water-proof layer (120), the water-absorbent layer (130), the ink barrier layer (150), the second water-proof layer (160) and second durable coating layer (160-1) may be omitted.

If absorption of water is required to take place through the front surface of the ink layer (140), the first adhesive layer (110-1), the first durable coating layer (120-1) and the first water-proof layer (120) are omitted, and the water-absorbent layer (130) may be formed or omitted.

Furthermore, if absorption of water is required to take place through the front surface of the ink layer (140) even in various inferior environments such repetitive friction etc., in which wear resistance is required, a space for checking of the ingress of water is formed by partially breaking the first durable coating layer (120-1) and the first water-proof layer (120) by irradiation of laser beam.

The water-ingress label of double coating capsule structure of the present invention may be formed by printing the label directly on various products, if necessary.

Any one or plural ones of resin stabilizing agent, slip agent, flame retardant material, dispersant, antimicrobial, leveling material, wetting material, plasticizer, filler, nucleating agent, water repellent, laser flair, moisture absorbent, de-foaming agent, coupling agent, antioxidant, ultraviolet ray absorbent, ultraviolet ray blocking agent, wax, or other additive etc. may be added to the ink used for the water-absorbent layer (130), the ink layer (140), the ink barrier layer (150), the first durable coating layer (120-1), the second durable coating layer (160-1), the first water-proof layer (120) and the second water-proof layer (160).

Then, for the colorant of the above-mentioned layers, one of dispersion dye, reactive dye, natural dye, synthetic dye, direct dye or other dye, monoazo-based pigment, phthalocyanine-based pigment, disazo-based pigment, azine-based pigment or other pigment, black carbon, pearl, filler, metal, silica, metallic oxides, mica or other colorant or mixture of plural ones thereof may be used.

There are various embodiments of the water-ingress label produced as above depending on its application, wherein the first adhesive layer (110-1) is formed on the front surface of the first durable coating layer (120-1) and the first release layer (110) is formed for protecting the first adhesive layer (110-1). The produced water-ingress label is used by detaching the first release layer (110) and thereafter attaching the first adhesive layer (110-1) to a proper portion of various products.

Furthermore, on the back surface of the second durable coating layer (160-1), the second adhesive layer (170-1) and the second release layer (170) may be formed to be used.

Meanwhile, if necessary, only one or both of a first pair of the first release layer (110) and the first adhesive layer (110-1) and a second pair of the second release layer (170)

and the second adhesive layer (170-1) may formed to be used, or both of the pairs may be omitted according to circumstances.

Figure 5:
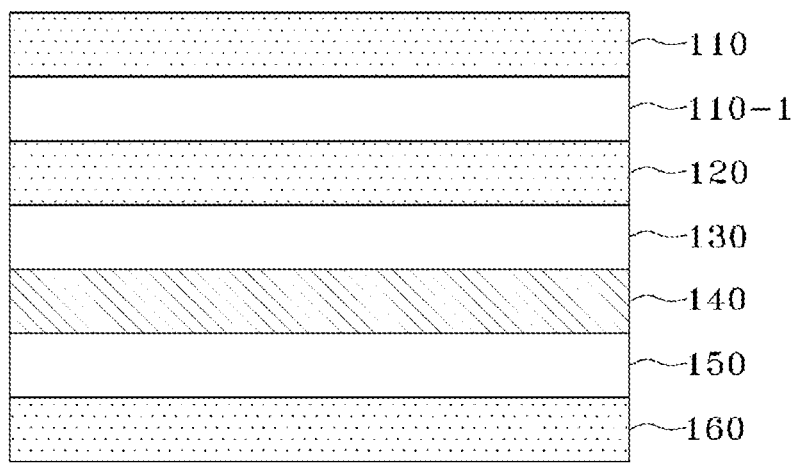
Figure 6:
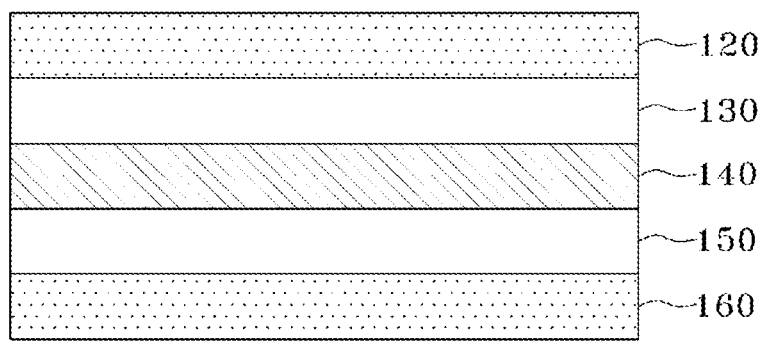

Namely, the water-ingress label of the present invention may be selectively constructed according to FIGS. 4 to 6 attached. As seen in FIG. 4 attached, the water-ingress label may be constructed in such a way that the second release layer (170) and the second adhesive layer (170-1) are omitted and only the first release layer (110) and the first adhesive layer (110-1) are formed. In another embodiment, as seen in FIG. 5 attached, the water-ingress label may be constructed in such a way that the first release layer (110) and the first adhesive layer (110-1) are omitted and only the second release layer (170) and the second adhesive layer (170-1) are formed.

Furthermore, as seen in FIG. 6 attached, the water-ingress label may be selectively constructed in such a way that the first release layer (110), the first adhesive layer (110-1), the second release layer (170) and the second adhesive layer (170-1) are each omitted.

By the above procedure, the double coating capsule water-ingress label completed in the form of roll, sheet or piece may be used with characters, patterns, logs, barcodes or external shape etc. imparted to the label by means of various printing, laser marking or die-cutting.

The completed product is diversely used for various electric and electronic products, medical supplies, seeds, foods, valuables, security articles, usual household items, other products etc.

Furthermore, the size, shape etc. of the completed product are properly determined depending on the form of object to which the label will be attached, and it is also possible to properly form and use the adhesive layers for attachment in the form of an entire surface, dots, stripes or partial shape.

As above, preferred exemplary embodiments of the present invention have been described through the specification and the drawings. Although specific terms are used, these are used in general meanings only for easily describing the technical contents of the present invention and helping to understand the present invention and are not intended to limit the scope of the present invention. It is obvious to a person skilled in the art that another modified examples may be implemented based on technical concepts of the present invention, aside from the exemplary embodiments disclosed herein.

DESCRIPTION OF REFERENCE NUMERALS

| | |
|---|---|
| 110: first release layer | 110-1: first adhesive layer |
| 120: first water-proof layer | 120-1: first durable coating layer |
| 130: water-absorbent layer | 140: ink layer |
| 105: ink barrier layer | 160: second water-proof layer |
| 160-1: second durable coating layer | 170-1: second adhesive layer |
| 170: second release layer | |

What is claimed:

1. A water-ingress label using a double coating capsule structure, wherein the water-ingress label comprises:
   a first release layer for protecting an adhesive layer;
   a first adhesive layer formed on a back surface of the first release layer for attachment to various products;
   a first durable coating layer formed on a back surface of the first adhesive layer for protection from the outside environment;
   a first water-proof layer formed on a back surface of the first durable coating layer in order to prevent absorption of water from the outside;
   a water-absorbent layer formed on a back surface of the first water-proof layer from any one of paper, synthetic paper, nonwoven fabric, synthetic nonwoven fabric, Korean paper and an absorbent coating in order to absorb the water from the outside;
   an ink layer formed by printing, on a back surface of the water-absorbent layer, an ink with a double coating capsule structure comprising a colorant consisting of any one or plural ones of water-soluble dyes, pigments, metal, silica, metallic oxides and mica, and a hydrophilic water-absorbent halogen-free resin;
   an ink barrier layer having a damp-proofing and water-proofing function, which is formed on a back surface of the ink layer and prevents leaking, through the back surface of the ink layer, of the colorant of any one or plural ones of the water-soluble dyes, pigments, metal, silica, metallic oxides and mica;
   a second water-proof layer formed on a back surface of the ink barrier layer in order to reinforce the ink barrier layer;
   a second durable coating layer formed on a back surface of the second water-proof layer for protection from the outside environment;
   a second adhesive layer formed a back surface of the second durable coating layer for attachment to various products; and
   a second release layer formed on a back surface of the second adhesive layer.

2. The water-ingress label using a double coating capsule structure according to claim 1, wherein the double coating capsule is formed of 15~35 wt. % of the colorant consisting of any one or plural ones of the water-soluble dyes, pigments, metal, silica, metallic oxides and mica; 15~25 wt. % of the hydrophilic water-absorbent halogen-free resin; 1~5 wt. % of crosslinking agent consisting of any one or plural ones of polyisocyanate-based resin, amino-based resin, aziridine-based resin, amide-based resin and epoxy-based resin; and 35~69 wt. % of solvent.

3. The water-ingress label using a double coating capsule structure according to claim 1, wherein the ink of the ink layer is formed of 15~35 wt. % of the double coating capsule; 15~25 wt. % of the halogen-free resin comprising resin consisting of any one or plural ones of polyamide-based resin, polyacryl-based resin, cellulose-based resin, polyester urethane-based resin, acryl-styrene copolymer resin and epoxy-based resin mixed with the colorant consisting of any one or plural ones of the dyes, pigments, metal, silica, metallic oxides and mica; and 40~70 wt. % of the solvent.

4. The water-ingress label using a double coating capsule structure according to claim 1, wherein the double coating capsule is formed solvent-resistant, damp-proofing and water-soluble.

5. The water-ingress label using a double coating capsule structure according to claim 4, wherein the double coating capsule is resistant to humidity, however, if absorbing the water, is expanded and thus broken, and then the contained colorant consisting of any one or plural ones of the water-soluble dyes, pigments, metal, silica, metallic oxides and mica is absorbed by the ink layer or by the ink layer and water-absorbent layer, thereby coloring the layers, and thus indication of the ingress of water is realized.

6. The water-ingress label using a double coating capsule structure according to claim 1, wherein in order for the water to be absorbed through a front surface of the ink layer even in an inferior outside environment, a partial space for checking of the ingress of water is formed by breaking the first durable coating layer and the first water-proof layer by irradiation of a specific partial laser beam or a partial space for checking of the ingress of water is formed by breaking the first durable coating layer, the first water-proof layer and the water-absorbent layer by irradiation of a specific partial laser beam.

7. The water-ingress label using a double coating capsule structure according to claim 6, wherein water-proof coating halogen-free resin for forming the ink barrier layer, the first water-proof layer and the second water-proof layer is formed of acryl resin, polyurethane resin, polystyrene resin, polyester resin, epoxy resin, silicone resin, polyethylene terephthalate resin and polypropylene resin.

8. The water-ingress label using a double coating capsule structure according to claim 6, wherein water-proof coating halogen-free ink for forming the ink barrier layer, the first water-proof layer and the second water-proof layer is formed by mixing 15~35 wt. % of the water-proof coating resin with 0~15 wt. % of the colorant consisting of any one or plural ones of the dyes, pigments, metal, silica, metallic oxides and mica and 50~85 wt. % of the solvent.

9. The water-ingress label using a double coating capsule structure according to claim 1, wherein the absorptive coating halogen-free ink for forming the water-absorbent layer is formed of 15~35 wt. % of the hydrophilic water-absorbent resin; 0~15 wt. % of the colorant consisting of any one or plural ones of the dyes, pigments, metal, silica, metallic oxides and mica; 0.1~5 wt. % of hardening agent consisting of any one of plural ones of amino resin, urethane hardening agent, aziridine, epoxy resin and amine-based hardening agent; and 45~84.9 wt. % of solvent.

10. The water-ingress label using a double coating capsule structure according to claim 1, wherein the absorptive coating resin for forming the water-absorbent layer is halogen-free urethane resin combined with acryl-based resin and polyester-ether copolymer resin, and is formed of any one or plural ones of the acryl-based resin, polyester-ether copolymer resin and urethane resin which are comprised of hydrophilic monomer, water-absorbent monomer and hydrophobic monomer for increasing the strength of coating film and preventing water solubility thereof.

11. The water-ingress label using a double coating capsule structure according to claim 10, wherein the absorptive coating resin for forming the water-absorbent layer is hydrophilic water-soluble halogen-free resin, and is formed of any one or plural ones of polyvinyl alcohol, polyvinyl pyrolidone, polyethylen glycol, methyl cellulose and carboxymethyl cellulose.

12. The water-ingress label using a double coating capsule structure according to claim 10, wherein in case of forming the water-absorbent layer as absorptive coating, any one of a front surface of the first durable coating layer, the first durable coating layer, the first water-proof layer, the ink barrier layer, the second water-proof layer, the second durable coating layer and the back surface of the second durable coating layer is formed from a substrate of film or release film.

13. The water-ingress label using a double coating capsule structure according to claim 12, wherein durable coating layer halogen-free ink for forming the first durable coating layer and the second durable coating layer is formed by mixing 15~35 wt. % of the halogen-free urethane resin able to easily protect the surface and block the moisture with 0~15 wt. % of the colorant consisting of any one or plural ones of the dyes, pigments, metal, silica, metallic oxides and mica; 1~5 wt. % of the hardening agent consisting of any one or plural ones of amino resin, urethane hardening agent, aziridine, epoxy resin and amine-based hardening agent; and 45~84 wt. % of the solvent.

14. The water-ingress label using a double coating capsule structure according to claim 13, wherein the durable coating layer resin for forming the first durable coating layer and the second durable coating layer is the halogen-free urethane resin combined with acryl-polyester resin, and is formed of any one or plural ones of acryl resin, polyester resin, epoxy resin, UV resin, polyether resin, silicone resin and unsaturated polyester resin.

* * * * *